(12) United States Patent
Nikou et al.

(10) Patent No.: US 11,284,951 B2
(45) Date of Patent: Mar. 29, 2022

(54) SYSTEMS AND METHODS FOR NAVIGATION AND CONTROL OF AN IMPLANT POSITIONING DEVICE

(71) Applicant: Blue Belt Technologies, Inc., Pittsburgh, PA (US)

(72) Inventors: Constantinos Nikou, Monroeville, PA (US); Branislav Jaramaz, Pittsburgh, PA (US); Benjamin Oliver McCandless, Pittsburgh, PA (US)

(73) Assignee: Blue Belt Technologies, Inc., Pittsburgh, PA (US)

( * ) Notice: Subject to any disclaimer, the term of this patent is extended or adjusted under 35 U.S.C. 154(b) by 197 days.

(21) Appl. No.: 16/690,892

(22) Filed: Nov. 21, 2019

(65) Prior Publication Data

US 2020/0085521 A1    Mar. 19, 2020

Related U.S. Application Data

(63) Continuation of application No. 16/043,691, filed on Jul. 24, 2018, now abandoned, which is a
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/10* (2016.02); *A61F 2/4609* (2013.01); *A61B 34/00* (2016.02);
(Continued)

(58) Field of Classification Search
CPC ..................................................... A61B 34/00
See application file for complete search history.

(56) References Cited

U.S. PATENT DOCUMENTS

| 5,007,936 A | 4/1991 | Woolson |
| 5,086,401 A | 2/1992 | Glassman et al. |

(Continued)

FOREIGN PATENT DOCUMENTS

| DE | 102006030343 A1 | 4/2008 |
| WO | 2014074676 A2 | 5/2014 |

OTHER PUBLICATIONS

Amstutz et al. "Range of Motion Studies for Total Hip Replacements" (Sep. 1975) Clinical Orthopaedics and Related Research 111:124-130.

(Continued)

*Primary Examiner* — Jacqueline Woznicki
(74) *Attorney, Agent, or Firm* — DLA Piper LLP

(57) ABSTRACT

Systems and methods for navigation and control of an implant positioning device are discussed. For example, a method can include operations for accessing an implant plan, establishing a 3-D coordinate system, receiving tracking information, generating control signals, and sending the control signals to the implant positioning device. The implant plan can include location and orientation data describing an ideal implant location and orientation in reference to an implant host. The 3-D coordinate system can provide spatial orientation for the implant positioning device and the implant host. The tracking information can identify current location and orientation data within the 3-D coordinate system for the implant positioning device and implant host during a procedure. The control signals can control operation of the implant positioning device to assist a surgeon in positioning the implant according to the implant plan.

7 Claims, 11 Drawing Sheets

Related U.S. Application Data continuation of application No. 14/073,999, filed on Nov. 7, 2013, now abandoned.

(60) Provisional application No. 61/724,601, filed on Nov. 9, 2012.

(51) Int. Cl.

| *A61B 34/32* | (2016.01) |
|---|---|
| *A61F 2/46* | (2006.01) |
| *A61B 34/10* | (2016.01) |
| *A61F 2/30* | (2006.01) |
| *A61B 34/20* | (2016.01) |

(52) U.S. Cl.
CPC .............. *A61B 34/20* (2016.02); *A61B 34/32* (2016.02); *A61B 34/70* (2016.02); *A61B 2034/104* (2016.02); *A61B 2034/2046* (2016.02); *A61B 2034/2055* (2016.02); *A61B 2034/301* (2016.02); *A61F 2/46* (2013.01); *A61F 2/4603* (2013.01); *A61F 2002/30538* (2013.01); *A61F 2002/4625* (2013.01); *A61F 2002/4627* (2013.01); *A61F 2002/4628* (2013.01); *A61F 2002/4632* (2013.01); *A61F 2002/4633* (2013.01); *A61F 2002/4681* (2013.01); *A61F 2002/4688* (2013.01)

(56) References Cited

U.S. PATENT DOCUMENTS

| 5,251,127 | A | 10/1993 | Raab |
|---|---|---|---|
| 5,299,288 | A | 3/1994 | Glassman et al. |
| 5,305,203 | A | 4/1994 | Raab |
| 5,353,385 | A | 10/1994 | Joskowicz et al. |
| 5,408,409 | A | 4/1995 | Glassman et al. |
| 5,571,110 | A | 11/1996 | Matsen, III et al. |
| 6,205,411 | B1 | 3/2001 | DiGioia, III et al. |
| 6,757,582 | B2 | 6/2004 | Brisson et al. |
| 8,206,405 | B2 | 6/2012 | Beverland et al. |
| 9,468,538 | B2 * | 10/2016 | Nycz .................. A61F 2/4607 |
| 9,585,725 | B2 | 3/2017 | Bonutti |
| 9,724,165 | B2 | 8/2017 | Arata et al. |
| 2002/0107573 | A1* | 8/2002 | Steinberg ................ A61F 2/441 623/17.12 |
| 2002/0183851 | A1 | 12/2002 | Spiegelberg et al. |
| 2003/0153978 | A1 | 8/2003 | Whiteside |
| 2005/0101962 | A1 | 5/2005 | Schwenke et al. |
| 2005/0149050 | A1 | 7/2005 | Stifter et al. |
| 2005/0203384 | A1 | 9/2005 | Sati et al. |
| 2006/0052691 | A1 | 3/2006 | Hall et al. |
| 2006/0235290 | A1 | 10/2006 | Gabriel et al. |
| 2011/0082462 | A1* | 4/2011 | Suarez .................. A61F 2/4607 606/99 |
| 2012/0157887 | A1 | 6/2012 | Fanson et al. |
| 2013/0060278 | A1 | 3/2013 | Bozung et al. |
| 2013/0161050 | A1 | 6/2013 | Pedicini |
| 2013/0296737 | A1 | 11/2013 | McMillan et al. |
| 2015/0182351 | A1 | 7/2015 | Behzadi |

OTHER PUBLICATIONS

Chinese Office Action CN20130058810.6 dated Feb. 6, 2017.
Chinese Office Action CN201480027135.5 dated Jan. 17, 2017.
Cobb et al. "The elevated-rim acetabular liner in total hip arthroplasty: Relationship to postoperative dislocation" (Jan. 1996) Journal of Bone and Joint Surgery 78-A(1):80-86.
International Search Report and Written Opinion for PCT/US2013/068876 dated May 9, 2015.
Japanese Office Action dated Nov. 28, 2016 for Japan Patent Application No. 2015-541887.
Krushell et al. "Elevated-rim Acetabular Components: Effect on Range of Motion and Stability in Total Hip Arthroplasty" (Oct. 1991) The Journal of Arthroplasty 6(supp):1-6.
Krushell et al. "Range of Motion in Contemporary total Hip Arthroplasty (the impact of modular head-neck components)" (Feb. 1991) The Journal of Arthroplasty 6:97-101.
Lewinnek et al. "Dislocations after total hip-replacement arthroplasties" (Mar. 1978) Journal of Bone and Joint Surgery 60-A(2):217-220.
Maxian et al. "Femoral head containment in total hip arthroplasty: Standard vs. extended lip liners" (Feb. 19-22, 1996) 42nd Annual Meeting of Orthopaedic Research Society, Atlanta, Georgia, p. 420.
Maxian et al. "Finite element modeling of dislocation propensity in total hip arthroplasty" (Feb. 19-22, 1996) 42nd Annual Meeting of Orthopaedic Research Society, Atlanta, Georgia, p. 259-264.
McCollum et al. "Dislocation after total hip arthroplasty (causes and prevention)" (1990) Clinical Orthopaedics and Related Research 261:159-170.
Morrey "Reconstructive Surgery of the Joints" (1996) Chapter—Joint Replacement Arthroplasty, Churchill Livingston Publishing, pp. 605-608.
Murphy et al. "Image-Guided Surgical Navigation: Basic Principles and Applications to Reconstructive Surgery" (2002) Beth Israel-Deaconess Medical Center, New Eng. Bapt. Bone and Joint Institute, Harvard Medical School, pp. 68-70.
Nolte "Basic Principles of COAS" (Jun. 2004) Injury, Int. J. Care Injured 35(1)supp:6-16.

* cited by examiner

SECTION A-A

SYSTEMS AND METHODS FOR NAVIGATION AND CONTROL OF AN IMPLANT POSITIONING DEVICE

CROSS-REFERENCE TO RELATED APPLICATION

This patent application is a continuation application of U.S. patent application Ser. No. 16/043,691, filed on Jul. 24, 2018, and titled "Systems and Methods for Navigation and Control of an Implant Positioning Device," which is itself a continuation application of U.S. patent application Ser. No. 14/073,999, filed on Nov. 7, 2013, and titled "Systems and Methods for Navigation and Control of an Implant Positioning Device," which claims the benefit of U.S. Provisional Application No. 61/724,601, titled "Systems and Method for Navigation and Control of an Implant Positioning Device," filed Nov. 9, 2012, each of which is incorporated herein by reference in its entirety.

TECHNICAL FIELD

This application relates generally to semi-active surgical robotics, and more specifically to systems and methods to provide computer-aided navigation and control of an implant positioning device.

BACKGROUND

The use of computers, robotics, and imaging to aid orthopedic surgery is well known in the art. There has been a great deal of study and development of computer-aided navigation and robotics systems used to guide surgical procedures. Two general types of semi-active surgical robotics have emerged and have been applied to orthopedic procedures, such as joint arthroplasty. The first type of semi-active robotics attach the surgical tool to a robotic arm that resists movements by the surgeon that deviate from a planned procedure, such as a bone resection. This first type often goes by the term haptic or haptics, which is derived from the Greek word for touch. The second type of semi-active robotics is focused on controlling aspects of the surgical tool, such as speed of a cutting bit. This second type of semi-active robotics is sometimes referred to as free-hand robotics, as a robotic arm does not restrict the surgeon.

Both types of surgical robotics utilize navigation or tracking systems to closely monitor the surgical tool and the patient during a procedure. The navigation system can be used to establish a virtual three dimensional (3-D) coordinate system, within which both the patient and the surgical device will be tracked.

Hip replacement is an area where the use of surgical robotics, advanced imaging, and computer-aided navigation are gaining acceptance. Total hip replacement (THR) or arthroplasty (THA) operations have been performed since the early 1960s to repair the acetabulum and the region surrounding it and to replace the hip components, such as the femoral head, that have degenerated. Currently, approximately 200,000 THR operations are performed annually in the United States alone, of which approximately 40,000 are redo procedures, otherwise known as revisions. The revisions become necessary due to a number of problems that may arise during the lifetime of the implanted components, such as dislocation, component wear and degradation, and loosening of the implant from the bone.

Dislocation of the femoral head from the acetabular component, or cup, is considered one of the most frequent early problems associated with THR, because of the sudden physical and emotional hardship brought on by the dislocation. The incidence of dislocation following the primary THR surgery is approximately 2-6% and the percentage is even higher for revisions. While dislocations can result from a variety of causes, such as soft tissue laxity and loosening of the implant, the most common cause is impingement of the femoral neck with either the rim of an acetabular cup implant, or the soft tissue or bone surrounding the implant. Impingement most frequently occurs as a result of mispositioning of the acetabular cup component within the pelvis.

Some clinicians and researchers have found incidence of impingement and dislocations can be lessened if the cup is oriented specifically to provide for approximately 15° of anteversion and 45° of abduction; however, this incidence is also related to the surgical approach. For example, McCollum et al. cited a comparison of THAs reported in the orthopaedic literature that revealed a much higher incidence of dislocation in patients who had THAs with a posterolateral approach. McCollum, D. E. and W. J. Gray, "Dislocation after total hip arthroplasty (causes and prevention)", Clinical Orthopaedics and Related Research, Vol. 261, p. 159-170 (1990). McCollum's data showed that when the patient is placed in the lateral position for a posterolateral THA approach, the lumbar lordotic curve is flattened and the pelvis may be flexed as much as 35°. If the cup was oriented at 15°-20° of flexion with respect to the longitudinal axis of the body, when the patient stood up and the postoperative lumbar lordosis was regained, the cup could be retroverted as much as 10°-15° resulting in an unstable cup placement. Lewinnek et al. performed a study taking into account the surgical approach utilized and found that the cases falling in the zone of 15°±10° of anteversion and 40°±10° of abduction have an instability rate of 1.5%, compared with a 6% instability rate for the cases falling outside this zone. Lewinnek G. E., et al., "Dislocation after total hip-replacement arthroplasties", Journal of Bone and Joint Surgery, Vol. 60-A, No. 2, p. 217-220 (March 1978). The Lewinnek work essentially verifies that dislocations can be correlated with the extent of malpositioning, as would be expected. The study does not address other variables, such as implant design and the anatomy of the individual, both of which are known to greatly affect the performance of the implant.

The design of the implant significantly affects stability as well. A number of researchers have found that the head-to-neck ratio of the femoral component is the key factor of the implant impingement, see Amstutz H. C., et al., "Range of Motion Studies for Total Hip Replacements", Clinical Orthopaedics and Related Research Vol. 111, p. 124-130 (September 1975). Krushell et al. additionally found that certain long and extra long neck designs of modular implants can have an adverse effect on the range of motion. Krushell, R. J., Burke D. W., and Harris W. H., "Range of motion in contemporary total hip arthroplasty (the impact of modular head-neck components)", The Journal of Arthroplasty, Vol. 6, p. 97-101 (February 1991). Krushell et al. also found that an optimally oriented elevated-rim liner in an acetabular cup implant may improve the joint stability with respect to implant impingement. Krushell, R. J., Burke D. W., and Harris W. H., "Elevated-rim acetabular components: Effect on range of motion and stability in total hip arthroplasty", The Journal of Arthroplasty, Vol. 6 Supplement, p. 1-6, (October 1991). Cobb et al. have shown a statistically significant reduction of dislocations in the case of elevated-rim liners, compared to standard liners. Cobb T. K., Morrey B. F., Ilstrup D. M., "The elevated-rim acetabular liner in total hip arthroplasty: Relationship to postoperative dislocation", Journal of Bone and Joint Surgery, Vol 78-A, No. 1, p. 80-86, (January 1996). The two-year probability of dislocation was 2.19% for the elevated liner, compared with 3.85% for standard liner. Initial studies by Maxian et al. using a finite element model indicate that the contact stresses and therefore the polyethylene wear are not significantly increased for elevated rim liners; however, points of impingement and subsequent angles of dislocation for different liner designs are different, as would be expected. Maxian T. A., et al. "Femoral head containment in total hip arthroplasty: Standard vs. extended lip liners", 42nd Annual meeting, Orthopaedic Research society, p. 420, Atlanta, Ga. (Feb. 19-22, 1996); and Maxian T. A., et al. "Finite element modeling of dislocation propensity in total hip arthroplasty", 42nd Annual meeting, Orthopaedic Research society, p. 259-64, Atlanta, Ga. (Feb. 19-22, 1996).

An equally important concern in evaluating the dislocation propensity of an implant is variations in individual anatomies. As a result of anatomical variations, there is no single optimal design and orientation of hip replacement components and surgical procedure to minimize the dislocation propensity of the implant. For example, the pelvis can assume different positions and orientations depending on whether an individual is lying supine (as during a CT-scan or routine X-rays), in the lateral decubitis position (as during surgery) or in critical positions during activities of normal daily living (like bending over to tie shoes or during normal gait). The relative position of the pelvis and leg when defining a "neutral" plane from which the angles of movement, anteversion, abduction, etc., are calculated will significantly influence the measured amount of motion permitted before impingement and dislocation occurs. Therefore, it is necessary to uniquely define both the neutral orientation of the femur relative to the pelvis for relevant positions and activities, and the relationship of the femur with respect to the pelvis of the patient during each segment of leg motion.

Currently, most planning for acetabular implant placement and size selection is performed using acetate templates and a single anterior-posterior x-ray of the pelvis. Acetabular templating is most useful for determining the approximate size of the acetabular component; however, it is only of limited utility for positioning of the implant because the x-rays provide only a two dimensional image of the pelvis. Also, the variations in pelvic orientation cannot be more fully considered as discussed above.

Intra-operative positioning devices currently used by surgeons attempt to align the acetabular component with respect to the sagittal and coronal planes of the patient. B. F. Money, editor, "Reconstructive Surgery of the Joints", chapter Joint Replacement Arthroplasty, pages 605-608, Churchill Livingston, 1996. These devices assume that the patient's pelvis and trunk are aligned in a known orientation, and do not take into account individual variations in a patient's anatomy or pelvic position on the operating room table. These types of positioners can lead to a wide discrepancy between the desired and actual implant placement, possibly resulting in reduced range of motion, impingement and subsequent dislocation.

Several attempts have been made to more precisely prepare the acetabular region for the implant components. U.S. Pat. No. 5,007,936 issued to Woolson is directed to establishing a reference plane through which the acetabulum can be reamed and generally prepared to receive the acetabular cup implant. The method provides for establishing the reference plane based on selecting three reference points, preferably the 12 o'clock position on the superior rim of the acetabulum and two other reference points, such as a point in the posterior rim and the inner wall, which are known distances from the superior rim. The location of the superior rim is determined by performing a series of computed tomography (CT) scans that are concentrated near the superior rim and other reference locations in the acetabular region.

In the Woolson method, calculations are then performed to determine a plane in which the rim of the acetabular cup should be positioned to allow for a predetermined rotation of the femoral head in the cup. The distances between the points and the plane are calculated and an orientation jig is calibrated to define the plane when the jig is mounted on the reference points. During the surgical procedure, the surgeon must identify the 12 o'clock orientation of the superior rim and the reference points. In the preferred mode, the jig is fixed to the acetabulum by drilling a hole through the reference point on the inner wall of the acetabulum and affixing the jig to the acetabulum. The jig incorporates a drill guide to provide for reaming of the acetabulum in the selected plane.

A number of difficulties exist with the Woolson method. For example, the preferred method requires drilling a hole in the acetabulum. Also, visual recognition of the reference points must be required and precision placement of the jig on reference points is performed in a surgical setting. In addition, proper alignment of the reaming device does not ensure that the implant will be properly positioned, thereby establishing a more lengthy and costly procedure with no guarantee of better results. These problems may be a reason why the Woolson method has not gained widespread acceptance in the medical community.

In U.S. Pat. Nos. 5,251,127 and 5,305,203 issued to Raab, a computer-aided surgery apparatus is disclosed in which a reference jig is attached to a double self indexing screw, previously attached to the patient, to provide for a more consistent alignment of the cutting instruments similar to that of Woolson. However, unlike Woolson, Raab et al. employ a digitizer and a computer to determine and relate the orientation of the reference jig and the patient during surgery with the skeletal shapes determined by tomography.

Similarly, U.S. Pat. Nos. 5,086,401, 5,299,288 and 5,408,409 issued to Glassman et al. disclose an image directed surgical robotic system for reaming a human femur to accept a femoral stem and head implant using a robot cutter system. In the system, at least three locating pins are inserted in the femur and CT scans of the femur in the region containing the locating pins are performed. During the implanting procedure, the locating pins are identified on the patient, as discussed in col. 9, lines 19-68 of Glassman's '401 patent. The location of the pins during the surgery are used by a computer to transform CT scan coordinates into the robot cutter coordinates, which are used to guide the robot cutter during reaming operations.

While the Woolson, Raab and Glassman patents provide methods and apparatuses that further offer the potential for increased accuracy and consistency in the preparation of the acetabular region to receive implant components, none of these references provide minimally invasive assistance during the implant procedure.

In addition, both the Raab and Glassman methods and apparatuses require that fiducial markers be attached to the patient prior to performing tomography of the patients. Following the tomography, the markers must either remain attached to the patient until the surgical procedure is performed or the markers must be reattached at the precise locations to allow the transformation of the tomographic data to the robotic coordinate system, either of which is undesirable and/or difficult in practice.

Thus, in addition to a continued need to provide improved systems and methods to provide proper placement plans and joint preparation techniques to ensure optimal outcomes in terms of range of motion and usage, there exists a need for improved intra-operative implant placement systems and methods.

BRIEF DESCRIPTION OF THE DRAWINGS

Some embodiments are illustrated by way of example and not limitation in the figures of the accompanying drawings in which.

DEFINITIONS

Figure 1:
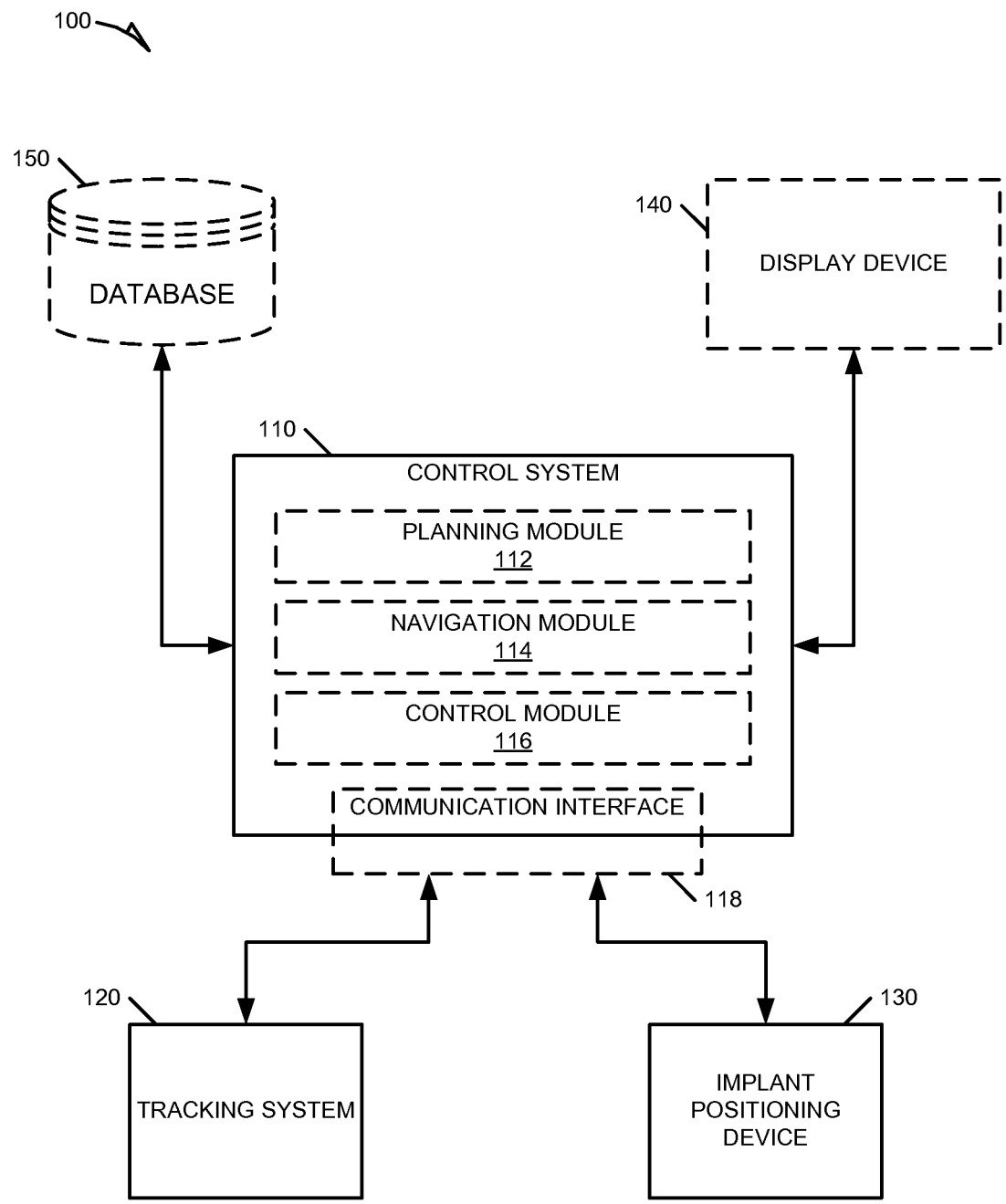
FIG. 1 is a block diagram depicting a system for providing navigation and control to an implant positioning device, according to an example embodiment.

Implant—For the purposes of this specification and the associated claims, the term "implant" is used to refer to a prosthetic device or structure manufactured to replace or enhance a biological structure. For example, in a total hip replacement procedure a prosthetic acetabular cup (implant) is used to replace or enhance a patients worn or damaged acetabulum. While the term "implant" is generally considered to denote a man-made structure (as contrasted with a transplant), for the purposes of this specification an implant can include a biological tissue or material transplanted to replace or enhance a biological structure.

Implant host—For the purposes of this specification and the associated claims, the term "implant host" is used to refer to a patient. In certain instances the term implant host may also be used to refer, more specifically, to a particular joint or location of the intended implant within a particular patient's anatomy. For example, in a total hip replacement procedure the implant host may refer to the hip joint of the patient being replaced or repaired.

Real-time—For the purposes of this specification and the associated claims, the term "real-time" is used to refer to calculations or operations performed on-the-fly as events occur or input is received by the operable system. However, the use of the term "real-time" is not intended to preclude operations that cause some latency between input and response, so long as the latency is an unintended consequence induced by the performance characteristics of the machine.

DETAILED DESCRIPTION

Example systems and methods for providing and using a navigated and computer controlled implant positioning device are described. In some example embodiments, the systems and methods for computer-aided navigation and control of an implant positioning device can involve a computer-controllable powered impactor. In an example, the computer-controllable powered impactor can be used by a surgeon to insert a prosthetic acetabular cup into the acetabulum of an implant host (e.g., a patient). In other examples, an alternative implant positioning device can be used to assist in a similar arthroplasty procedure, such as a total knee replacement. In the following description, for purposes of explanation, numerous specific details are set forth in order to provide a thorough understanding of example embodiments. It will be evident, however, to one skilled in the art, that the present invention may be practiced without these specific details. It will also be evident that a computer controlled implant positioning system is not limited to the examples provided and may include other scenarios not specifically discussed.

In an example, the discussed system includes an acetabular positioning device outfitted with additional impaction devices. The positioning device can be tracked in at least 2 degrees of rotation by a tracking system connected to a computer. Programs running on a control system can communicate with the tracking system to monitor the orientation and optionally the position of the acetabular implant as the user orients it relative to the patient's body (which is also tracked by the tracking system) in order to achieve an intended preoperative plan, which is stored in the control system's memory. The control system also can include a display that gives the user (e.g., surgeon) information regarding the current position and/or orientation relative to the body position, and/or relative to the preoperative plan. The control system can also communicate with the impaction device(s). A variety of algorithms may be used to calculate which and how impact devices should be activated. The simplest algorithm could be that the impact devices activate when the user aligns the acetabular implant coincident to the preoperative plan. Furthermore, this actuation could be dependent on secondary input from the user, like a trigger, foot pedal signal, or voice command.

The impaction devices may be mounted to the acetabular positioner such that the impactions apply forces or torques to the implant in a known way, and the computer algorithms may use robotic path planning techniques to optimize a sequence of impactions to push the acetabular component in an optimized pattern toward the final preoperative plan.

Additional sensors can be deployed on the positioning tool in order to give feedback on forces and torques applied to the positioning tool, or to measure the force and torque applied to a partially or fully fixed acetabular implant by the positioning device, which could affect the result of the impaction patterns that are employed.

Example System

FIG. 1 is a block diagram depicting a system 100 for providing navigation and control to an implant positioning device 130, according to an example embodiment. In an example, the system 100 can include a control system 110, a tracking system 120, and an implant positioning device 130. Optionally, the system 100 can also include a display device 140 and a database 150. In an example, these components can be combined to provide navigation and control of the implant positioning device 130 during an orthopedic (or similar) prosthetic implant surgery.

The control system 110 can include one or more computing devices configured to coordinate information received from the tracking system 120 and provide control to the implant positioning device 130. In an example, the control system 110 can include a planning module 112, a navigation module 114, a control module 116, and a communication interface 118. The planning module 112 can provide pre-operative planning services that allow clinicians the ability to virtually plan a procedure prior to entering the operating room. The background discusses a variety of pre-operative planning procedures used in total hip replacement (total hip arthroplasty (THA)) that may be used in surgical robotic assisted joint replacement procedures. Additionally, U.S. Pat. No. 6,205,411 titled "Computer-assisted Surgery Planner and Intra-Operative Guidance System," to Digioia et al., discusses yet another approach to pre-operative planning U.S. Pat. No. 6,205,411 is hereby incorporated by reference in its entirety.

In an example, such as THA, the planning module 112 can be used to manipulate a virtual model of the implant in reference to a virtual implant host model. The implant host model can be constructed from actual scans of the target patient, such as computed tomography (CT), magnetic resonance imaging (MRI), positron emission tomographic (PET), or ultrasound scanning of the joint and surround structure. Alternatively, the pre-operative planning can be performed by selecting a predefined implant host model from a group of models based on patient measurements or other clinician selected inputs. In certain examples, pre-operative planning is refined intra-operatively by measuring the patient's (target implant host's) actual anatomy. In an example, a point probe connected to the tracking system 120 can be used to measure the target implant host's actual anatomy.

In an example, the navigation module 114 can coordinate tracking the location and orientation of the implant, the implant host, and the implant positioning device 130. In certain examples, the navigation module 114 may also coordinate tracking of the virtual models used during pre-operative planning within the planning module 112. Tracking the virtual models can include operations such as alignment of the virtual models with the implant host through data obtained via the tracking system 120. In these examples, the navigation module 114 receives input from the tracking system 120 regarding the physical location and orientation of the implant positioning device 130 and an implant host. Tracking of the implant host may include tracking multiple individual bone structures. For example, during a total knee replacement procedure the tracking system 120 may individually track the femur and the tibia using tracking devices anchored to the individual bones.

In an example, the control module 116 can process information provided by the navigation module 114 to generate control signals for controlling the implant positioning device 130. In certain examples, the control module 116 can also work with the navigation module 114 to produce visual animations to assist the surgeon during an operative procedure. Visual animations can be displayed via a display device, such as display device 140. In an example, the visual animations can include real-time 3-D representations of the implant, the implant host, and the implant positioning device 130, among other things. In certain examples, the visual animations are color-coded to further assist the surgeon with positioning and orientation of the implant.

In an example, the communication interface 118 facilitates communication between the control system 110 and external systems and devices. The communication interface 118 can include both wired and wireless communication interfaces, such as Ethernet, IEEE 802.11 wireless, or Bluetooth, among others. As illustrated in FIG. 1, in this example, the primary external systems connected via the communication interface 118 include the tracking system 120 and the implant positioning device 130. Although not shown, the database 150 and the display device 140, among other devices, can also be connected to the control system 110 via the communication interface 118. In an example, the communication interface 118 communicates over an internal bus to other modules and hardware systems within the control system 110.

In an example, the tracking system 120 provides location and orientation information for surgical devices and parts of an implant host's anatomy to assist in navigation and control of semi-active robotic surgical devices. The tracking system 120 can include a tracker that includes or otherwise provides tracking data based on at least three positions and at least three angles. The tracker can include one or more first tracking markers associated with the implant host, and one or more second markers associated with the surgical device (e.g., an implant positioning device 130). The markers or some of the markers can be one or more of infrared sources, Radio Frequency (RF) sources, ultrasound sources, and/or transmitters. The tracking system 120 can thus be an infrared tracking system, an optical tracking system, an ultrasound tracking system, an inertial tracking system, a wired system, and/or a RF tracking system. One illustrative tracking system can be the OPTOTRAK® 3-D motion and position measurement and tracking system described herein, although those of ordinary skill in the art will recognize that other tracking systems of other accuracies and/or resolutions can be used.

U.S. Pat. No. 6,757,582, titled "Methods and Systems to Control a Shaping Tool," to Brisson et al., provides additional detail regarding the use of tracking systems, such as tracking system 120, within a surgical environment. U.S. Pat. No. 6,757,582 (the '582 patent) is hereby incorporated by reference in it's entirely.

In an example, a surgeon can use the implant positioning device 130 to assist in inserting an implant within an implant host during a surgical procedure. For example, within THA a surgeon will often insert a prosthetic acetabular cup into the implant host's acetabulum. Inserting a prosthetic acetabular cup often involves a manual or powered impaction device. When a manual impactor is used, the surgeon will hammer on the end of the impactor with a mallet to seat the artificial acetabular cup (e.g., implant) into the proper position. While some manual impaction devices have been coupled with tracking systems, such as tracking system 120, the assistance provided to the surgeon is limited to alignment of the manual impaction device. The systems currently available lack the ability to provide navigated control of an impaction device to assist the surgeon in getting the implant into the ideal implant location (as determined via preoperative and intra-operative planning) Additional details on an example navigated implant positioning device, such as implant positioning device 130, are provided below in reference to FIG. 7.

Example Operating Environment

Figure 2:
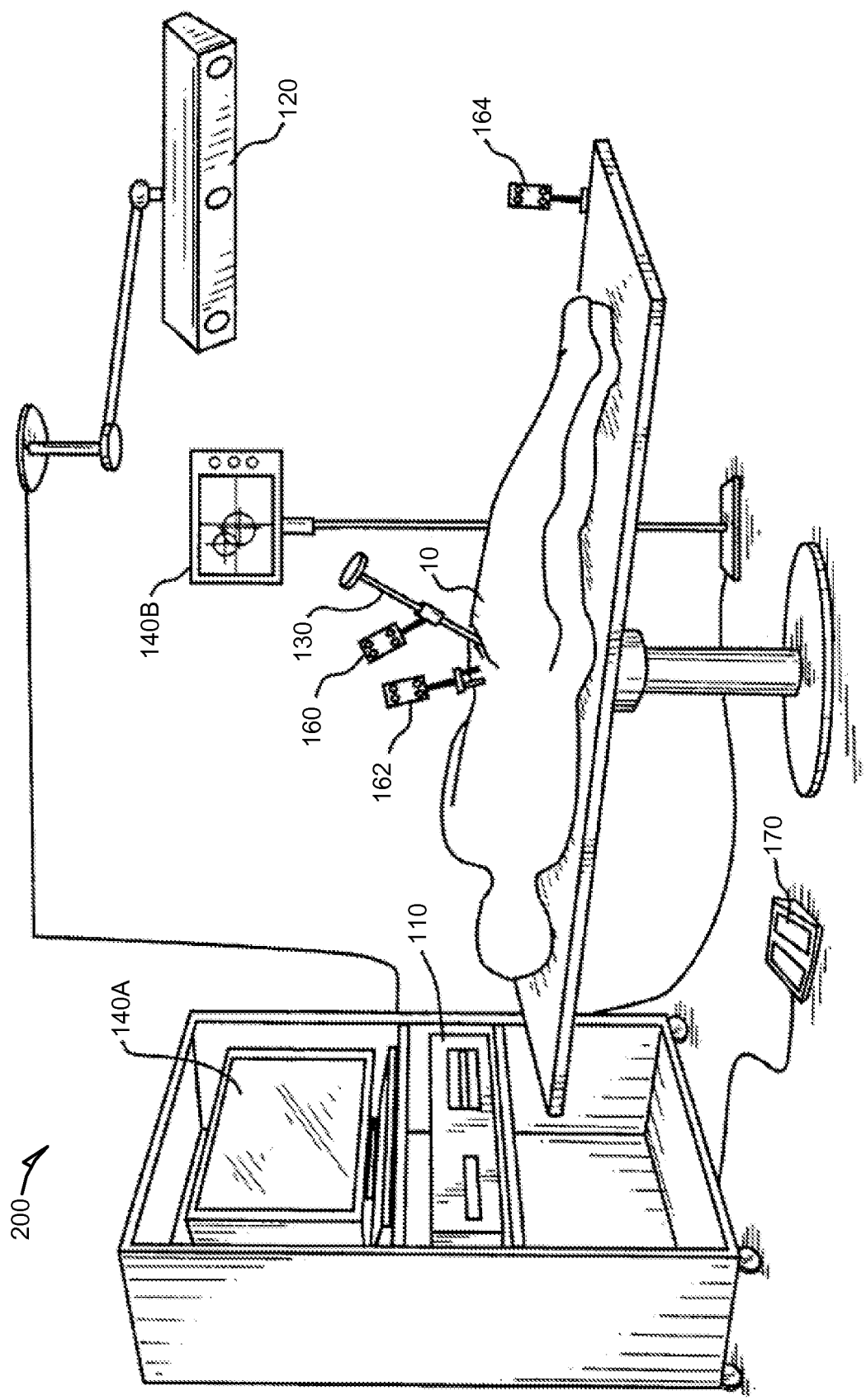
FIG. 2 is a diagram illustrating an environment for operating a system for navigation and control of an implant positioning device, according to an example embodiment.

FIG. 2 is a diagram illustrating an environment for operating a system 200 for navigation and control of an implant positioning device 130, according to an example embodiment. In an example, the system 200 can include components similar to those discussed above in reference to system 100. For example, the system 200 can include a control system 110, a tracking system 120, an implant positioning device 130, and one or more display devices, such as display device 140A and 140B. The system 200 also illustrates an implant host 10, tracking markers 160, 162, and 164, as well as a foot control 170.

In an example, the tracking markers 160, 162, and 164 can be used by the tracking system 120 to track location and orientation of the implant host 10, the implant positioning device 130, and a reference, such as an operating table (tracking marker 164). In this example, the tracking system 120 uses optical tracking to monitor the location and orientation of tracking markers 160, 162, and 164. Each of the tracking markers (160, 162, and 164) includes three or more tracking spheres that provide easily processed targets to determine location and orientation in up to six degrees of freedom. The tracking system 120 can be calibrated to provide a localized 3-D coordinate system within which the implant host 10 and the implant positioning device 130 (and by reference the implant) can be spatially tracked. For example, as long as the tracking system 120 can image three of the tracking spheres on a tracking marker, such as tracking marker 160, the tracking system 120 can utilize image processing algorithms to generate points within the 3-D coordinate system. Subsequently, the tracking system 120 (or the navigation module 114 (FIG. 1) within the control system 110) can use the 3 points to triangulate an accurate 3-D position and orientation associated with the device the tracking marker is affixed to, such as the implant host 10 or the implant positioning device 130. Once the precise location and orientation of the implant positioning device 130 is known, the system 200 can use the known properties of the implant positioning device 130 to accurately calculate a position and orientation associated with the implant (without the tracking system 120 being able to visualize the implant, which may be within the implant host 10 and not visible to the surgeon or the tracking system 120).

Operations and capabilities of the systems 100 (FIG. 1) and 200 are discussed further below in reference to FIGS. 3-6.

Example Methods

Figure 3:
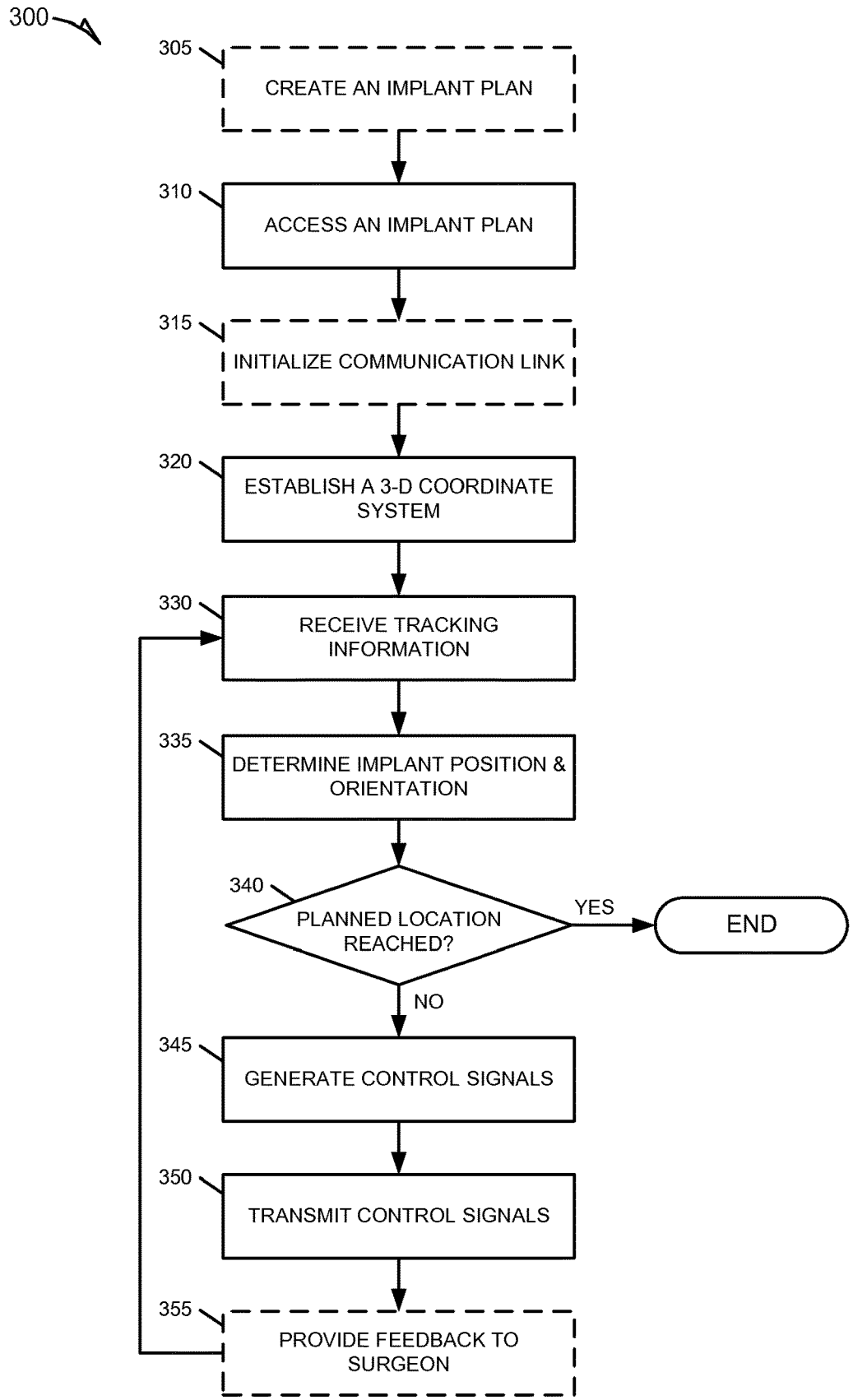
FIG. 3 is a flowchart illustrating a method for navigation and control of an implant positioning device, according to an example embodiment.

FIG. 3 is a flowchart illustrating a method 300 for navigation and control of an implant positioning device 130 (FIG. 2), according to an example embodiment. In an example, the method 300 can include operations for: accessing an implant plan at 310, establishing a 3-D coordinate system at 320, receiving tracking information at 330, determining implant position and orientation at 335, determining if a planned location has been reached at 340, generating control signals at 345, and transmitting control signals at 350. Optionally, the method 300 can also include operations such as creating an implant plan at 305, initializing a communication link at 315, and providing feedback to a surgeon at 355. In general, the operations discussed in reference to method 300 are performed within the control system 100 (FIG. 1). However, in certain examples, some of the operations may be performed within other components of systems 100 or 200, such as the tracking system 120 (FIG. 2). Additionally, in some examples, some of the recited operations may not be required to provide navigation and control to an implant positioning device 130 (FIG. 2).

In an example, the method 300 can optionally begin at 305 with the planning module 112 (FIG. 1) assisting a clinician in creating an implant plan. Creating an implant plan can include generating a virtual implant host model from CT, MRI, or similar medical scans of the appropriate anatomy of the implant host 10 (FIG. 2). Creating an implant plan can also include manipulation of a virtual implant model in reference to a virtual implant host model. Further, creating an implant plan can include planning bone shaping procedures to be performed prior to implant insertion within the implant host 10. In an example, the implant plan created in this operation can provide detailed location and orientation data regarding the ideal implant location within an implant host, such as implant host 10.

At 310, the method 300 can continue with the control system 110 (FIG. 1) accessing an implant plan, such as the implant plan created in operation 305. Alternatively, the control system 110 may access an implant plan stored in database 150 (FIG. 1). In an example, data regarding the implant, the desired (ideal) implant location, and the implant host 10 within the implant plan can be made available to the navigation module 114 and control module 116 as necessary to provide navigation and control to an implant positioning device, such as implant positioning device 130 (FIG. 2).

At 315, the method 300 can optionally continue with the control system 110, via the communication interface 118, initializing a communication link with the implant positioning device 130 and/or the tracking system 120 (FIG. 1). Initializing the communication link can, in certain examples, include verifying control capabilities of the implant positioning device 130. For example, the systems 100 and 200 (FIGS. 1 & 2) may be suitable for use with a computer-controlled powered impactor with or without extension capabilities, which provides a controllable telescoping extension for assisting with implant insertion. Initializing the communication link with the implant positioning device 130 can determine whether the connected device includes a powered extension capability.

At 320, the method 300 can continue with the control system 110 establishing a 3-D coordinate system to track the surgical instruments and implant host 10 (FIG. 2) during the procedure. In an example, the control system 110 works in conjunction with the tracking system 120 (FIG. 2) to establish a localized 3-D coordinate system. In certain examples, the control system 110 can step a clinician through alignment and calibration operations involving tracking markers, such as tracking markers 160, 162, and 164 (FIG. 2), to establish the 3-D coordinate system. Establishing the 3-D coordinate system may also involve use of a point probe associated with the tracking system 120. Further details regarding operation 320 are discussed below in reference to FIG. 4.

At 330, the method 300 can continue with the control system 110 receiving tracking information from the tracking system 120 (FIG. 1). In this example, at operation 330 the method 300 enters the intra-operative phase. Within the intra-operative phase surgical instruments, the implant host 10 (FIG. 2), and the implant can be tracked to assist a clinician in performing the surgical procedure. The tracking information received in operation 330 can include location and orientation information for components of the systems 100 or 200, such as the implant host 10 and the implant positioning device 130 (FIGS. 1 & 2). In other examples, the tracking information received in operation 330 can consist merely of reference points detected for each tracked component, such as identified locations of the tracking spheres on tracking marker 160 (FIG. 2). In these examples, the navigation module 114 (FIG. 1) can use the reference points to calculate location and orientation data associated with the tracked component.

In an example, at 335, the method 300 can continue with the navigation module 114 (FIG. 1) determining implant position and orientation. In certain other examples, determining implant position and orientation may be done within the tracking system 120 (FIG. 2). In an example, the implant position and orientation is calculated based on the known location and orientation of the implant positioning device 130 (FIG. 2) and the known relationship between the implant positioning device 130 and the implant. For example, the tracking system 120 can provide a point location and orientation within the 3-D coordinate system associated with the implant positioning device 130. Pre-operative calibration of the implant positioning device 130 can determine the relative position of an end effector of the implant positioning device 130, which allows a location and orientation of an implant affixed to the end effector to be determined. Calibrating this relationship allows for the navigation module 114 to track the precise location of the implant via receiving the tracked location of the implant positioning device 130.

At 340, the method 300 can continue with the control system 110 determining whether the implant has reached the planned (e.g., ideal) location in reference to the implant host 10 (FIG. 2). If the ideal implant location has been achieved, the method 300 can conclude. If the implant has not reached the ideal implant location, then at 345 the method 300 can continue with the control module 116 (FIG. 1) generating control signals to navigate and control the implant positioning device 130 (FIG. 2). Additional detail regarding control signal generation is discussed below in reference to FIG. 5.

At 350, the method 300 continues with the control module 116 transmitting, over the communication interface 118, the control signals to the implant positioning device 130 (FIG. 1). The process of receiving tracking information, determining implant location, generating control signals, and transmitting the control signals represented by operations 330 through 350 can occur as often as every few milliseconds, allowing the control system 110 (FIG. 2) to rapidly alter the control parameters sent to the implant positioning device 130. Cycles times provided herein are merely exemplary and may be altered by application of specialized processing hardware or optimized algorithms. Additionally, physical constraints such as vibration settling time may also affect the timing of control cycles in operation. The ability to rapidly alter the control parameters allows for accurate control over the placement and orientation of the implant within the implant host 10 (FIG. 2).

At 355, the method can optionally continue with the control system 110 (FIG. 2) providing feedback to the surgeon to further assist in positioning the implant. As discussed in greater detail below in reference to FIG. 6, the feedback provided to the surgeon can be visual, audible, and tactile.

As noted above, the method 300 can loop through operations 330-355 until it is determined, at operation 340, that the implant has reached the ideal location and orientation. In an example, the method 300 can also be halted or paused by a clinician during the implant procedure. If paused, the control system 110 (FIG. 2) can allow the clinician to continue the implant procedure. If the method 300 is halted, the clinician can be provided options for withdrawing the implant or leaving the implant in the position reached prior to halting the navigation and control method. In certain examples, the implant positioning device 130 (FIG. 2) can include a trigger actuator that can be configured to start and subsequently pause the operations discussed in reference to FIG. 3.

The following methods provide additional detail regarding operations introduced above in reference to FIG. 3. The operations discussed in the following methods are optional and may be performed in a different order or on different systems than those discussed in the following examples. Additionally, the operations discussed above in reference to FIG. 3 may not all be necessary to provide navigation and control to an implant positioning device, such as implant positioning device 130 (FIG. 2). Further, the order of operations discussed above is merely exemplary, the discussed operations may be performed in different orders and on different systems than discussed above.

Figure 4:
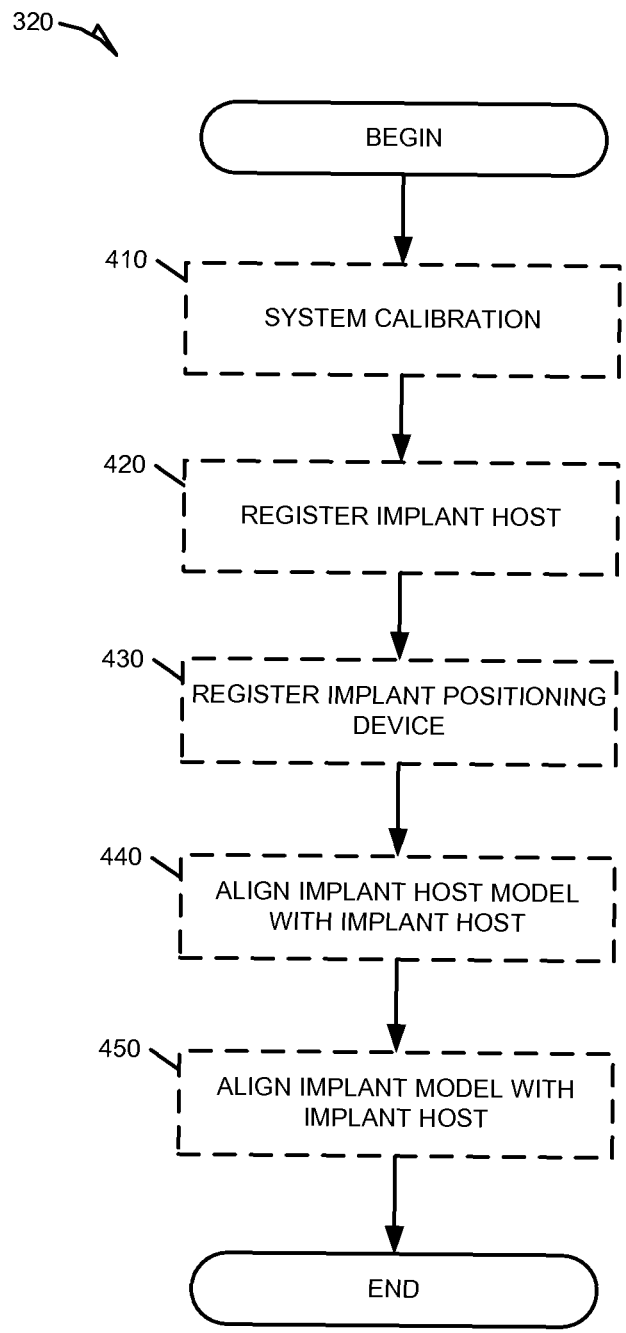
FIG. 4 is a flowchart illustrating a method for establishing a three dimensional coordinate system, according to an example embodiment.

FIG. 4 is a flowchart illustrating a method 320 for establishing a three dimensional (3-D) coordinate system, according to an example embodiment. In an example, the method 320 can include operations such as: system calibration at 410, registration of an implant host 10 at 420, registration of an implant positioning device 130 at 430, aligning an implant host model with an implant host 10 at 440, and aligning an implant model with an implant host 10 (FIG. 2) at 450. The method 320 corresponds to the operation 320 introduced is FIG. 3. The operations discussed in reference to method 320 represent an example embodiment of operation 320.

The method 320 can begin at operation 410 with the control system 110 and the tracking system 120 (FIG. 2) performing a system calibration. Calibration of the tracking system 120 enables precise tracking of tracking markers within the field of view of the tracking system 120. In an example, the tracking system 120 can include a point probe and a calibration fixture for calibrating the tracking system 120. The tracking system 120, or the control system 110 in conjunction with the tracking system 120, can step a clinician through calibration of a point probe using a calibration fixture. The calibration fixture can provide precise orientation of a 3-D coordinate system and the point probe can then be used to register (e.g., calibrate) other components to be tracked, such as an implant host 10 and an implant positioning device 130 (FIG. 2). The tracking system 120, or the control system 110 in conjunction with the tracking system 120, can step a clinician through calibration of a point probe optionally using a calibration fixture. The calibration process defines precise position and orientation of a 3-D coordinate system related to the point probe (especially at its tip). The probe can then be used to register (e.g., calibrate) other components to be tracked, such as an implant host 10 and an implant positioning device 130.

At 420, the method 320 can continue with the control system 110 facilitating registration of the implant host 10 with the tracking system 120 (FIG. 2). In an example, a tracking marker, such as tracking marker 162 (FIG. 2) can be affixed to the implant host 10. With the tracking marker affixed, the clinician can use a calibrated point probe to locate landmarks on the implant host 10 to register the critical anatomy with the tracking system 120. Registration provides the control system 110 and/or the tracking system 120 the information necessary to translate the position of the tracking marker 162 into location and orientations relative to the anatomy of the implant host 10 that will be involved in the surgical procedure. For example, in THA the registration procedure may locate relative locations of the implant host 10's acetabulum.

At 430, the method 320 can continue with the control system 110 and/or tracking system 120 facilitating registration of the implant positioning device 130 within the 3-D coordinate system established by the tracking system 120 (FIG. 2). In an example, registration of the implant positioning device 130 can include using a point probe calibrated to the 3-D coordinate system to locate landmark locations on the implant positioning device 130. Tracking system 120 uses location information for the tracking marker 160 (FIG. 2) attached to the implant positioning device 130 in conjunction with the landmark points identified by the point probe to register the critical dimensions and relative locations on the implant positioning device 130.

At 440, the method 320 can continue with the control system 110 aligning a virtual implant host model with the implant host 10 (FIG. 2). As discussed above, an implant plan can include a virtual implant host model, which can be used for pre-operative planning of implant location and orientation. In certain examples, the virtual implant host model can be aligned within the 3-D coordinate system established by the tracking system 120 to assist in navigation and control of the implant positioning device 130 (FIG. 2). Alignment of the virtual implant host model can be done from the landmark locations gathered on the implant host 10 during registration of the implant host 10. The aligned virtual implant host model can be used to assist the surgeon in visualizing the implant location through 3-D visualizations on a display device, such as display device 140 (FIG. 2).

At 450, the method 320 can continue with the control system 110 aligning a virtual implant model with the implant host 10 (FIG. 2). Similar to the virtual implant host model, the virtual implant model can be used during pre-operative planning to identify an ideal location for the implant within an implant host, such as implant host 10. In order to properly navigate and control the implant positioning device 130, the virtual implant model used for planning can be aligned within the 3-D coordinate system established by the tracking system 120 (FIG. 2) in the ideal location identified during planning. In certain examples, the virtual implant model can also be used to assist the surgeon in visualizing the implant location during the insertion procedure.

Figure 5:
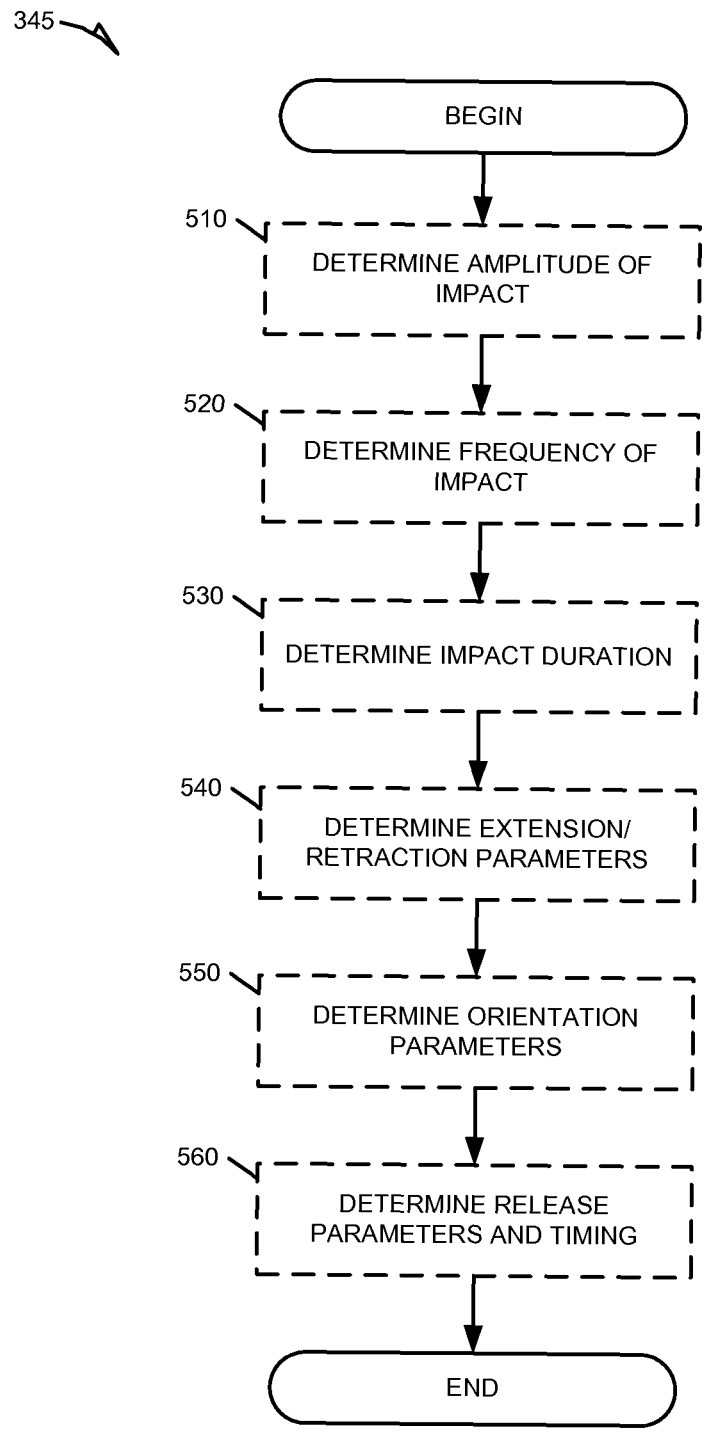
FIG. 5 is a flowchart illustrating a method for generating control signals to control an implant positioning device, according to an example embodiment.

FIG. 5 is a flowchart illustrating a method 345 for generating control signals to control an implant positioning device 130 (FIG. 2), according to an example embodiment. In an example, the method 345 can include operations such as: determining an amplitude of impact at 510, determining a frequency of impact at 520, determining a duration of impact at 530, determining extension or retraction parameters at 540, determining orientation parameters at 550, and determining release parameters and timing at 560. The control signal generation operations illustrated in FIG. 5 are directed towards a computer-controlled powered impaction device, such as the one described below in reference to FIG. 7. In examples using a different type of implant positioning device, a different set of control signal generation operations may be applicable.

In this example, the method 345 can begin at 510 with the control module 116 (FIG. 1) determining the amplitude of impact based on parameters such as current implant location and orientation in reference to the ideal implant location. Amplitude of impact is used here to refer to the magnitude of force applied by the implant positioning device 130 (FIG. 2) to the implant. At 520, the method 345 can continue with the control module 116 determining a frequency of impact to be sent to the implant positioning device 130. Frequency of impact is used here to refer to how often the implant positioning device 130 delivers an impact at the planned amplitude.

At 530, the method 345 can continue with the control module 116 (FIG. 1) determining duration of the impacts to be delivered with the current amplitude and frequency parameters. In another example, duration may be calculated to assist the clinician in determining how long a particular orientation of the implant positioning device 130 (FIG. 2) should be maintained. In certain examples, the control system 110 can utilize a pulse-measure-pulse-measure control scheme with varying durations related to the amplitude and frequencies being applied. In yet other examples, set impact durations may be used to keep the surgeon engaged in the alignment process and allow time to check progress between autonomous motions.

In certain examples, the implant positioning device 130 (FIG. 2) may include the ability to extent and/or retract a portion of the device. In these examples, the method 345 may include an operation 540. At 540, the method 345 can continue with the control module 116 (FIG. 1) determining extension or retraction parameters to send to the implant positioning device 130. For example, during insertion of a prosthetic acetabular cup with a computer-controlled powered impaction device, the device may be designed to allow the clinician to merely maintain a proper alignment, while the device extends an impaction head (e.g., end effector) with the implant into the proper location.

At 550, the method 345 can continue with the control module 116 determining orientation parameters to be sent to the implant positioning device 130 (FIG. 1). In certain examples, the implant positioning device 130 may have the ability to control orientation of the implant on the end effector. Such as in the example of a prosthetic acetabular cup, the end effector may be configured to allow impacts to be directed to localized portions on the circumference of the implant. Localizing impacts to a small portion of the circumference can induce a rotation force on the implant. In other examples, the end effector of the implant positioning device 130 may be able to pivot or rotate to facilitate other orientation adjustments.

Finally, at 560, the method 345 can conclude with the control module 116 (FIG. 1) determining release parameters and timing. In an example, the implant positioning device 130 (FIG. 2) can include a mechanism to release the implant once it has reached the ideal location. Release parameters can include parameters to instruct the implant positioning device 130 to release an implant retaining mechanism or trigger a release actuator to remove the implant from the end effector. In an example, a release actuator can include a simple air or electrically actuated cylinder within the end effector to release the implant.

Figure 6:
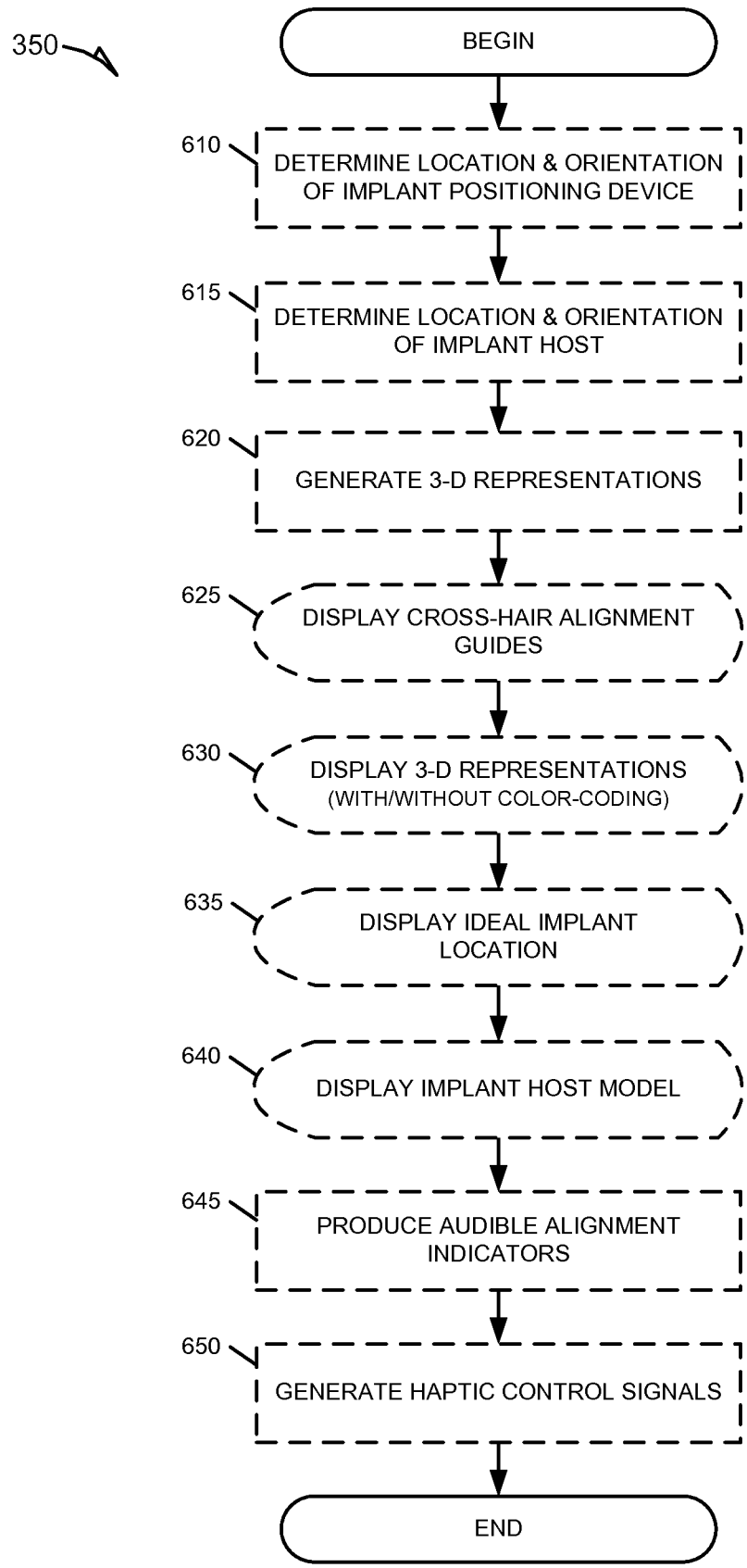
FIG. 6 is a flowchart illustrating a method for providing assistance to a surgeon operating an implant positioning device, according to an example embodiment.

FIG. 6 is a flowchart illustrating a method 350 for providing assistance to a surgeon operating an implant positioning device 130 (FIG. 2), according to an example embodiment. In an example, the method 350 can include operations such as: determining location and orientation of the implant positioning device 130 at 610, determining alignment and orientation of implant host 10 (FIG. 2) at 615, generating 3-D representations at 620, displaying cross-hair alignment guides at 625, displaying 3-D representations at 630, displaying ideal implant location at 635, displaying an implant host model at 640, producing audible alignment indicators at 645, and generating haptic control signals at 650. The following operations highlight one of the many potential benefits of computer-aided navigation and control, the ability to assist a clinician by visualizing aspects of an implant host 10's anatomy and the implant during a procedure where both may be partially or completely obstructed from view.

In an example, the method 350 can begin at 610 with the navigation module 114 determining location and orientation of the implant positioning device 130 (FIG. 1). In certain examples, the location and orientation of the implant positioning device 130 will have already been calculated to determine the location and orientation of the implant (see operation 335 in FIG. 3). At 615, the method 350 can continue with the navigation module 114 determining, if necessary, a location and orientation of the implant host 10 (FIG. 2). Like operation 610, operation 615 may have been performed previously to determine the implant location relative to the implant host 10.

At 620, the method 350 can continue with the control system 110 generating 3-D representations of components such as the implant and the implant positioning device 130 as well as the implant host 10 (FIG. 2). The representations generated may be used to present real-time visualizations to the surgeon. At 625, the method 350 can continue with the control system 110 generating and displaying cross-hair alignment guides to assist the surgeon in aligning the implant positioning device 130. In an example, information including the current implant location, the ideal (planned) implant location, location and orientation of the implant positioning device 130, and location orientation of the implant host 10 can be used to generate the cross-hair alignment guides. In an example, two (2) dimensions (e.g., x and y) on a cross-hair alignment display can correspond to the azimuth and elevation of the implant positioning device 130 in a spherical coordinate system aligned to the implant plan. The center of the XY plot corresponds to the implant plan, and the XY coordinates of the implant positioning device 130 are the azimuth and elevation differences between the implant positioning device 130 and implant plan. In certain scenarios, this definition may lead to a non-intuitive correlation between motion of the implant positioning device 130 and movement of the cross-hair on the screen. Therefore, angular reference planes may be aligned to global references, such as gravity or the user's facing direction. These references allow for the user's left to correspond to leftward motion on the screen, and motion in the upward direction (relative to gravity) of the implant positioning device 130 handle to upward motion of the cross-hair. Transformations of the reference coordinates in this manner are evident to those skilled in the art of robotics or surgical navigation.

At 625, the method 350 can continue with the control system 110 displaying 3-D representations on a display device, such as display device 140 (FIG. 2). In an example, the 3-D representations generated in operation 620 can be displayed to assist the surgeon in visualizing implant location and orientation of the implant positioning device 130 (FIG. 2), among other things. In some examples, the 3-D visualizations can be color-coded to provide additional feedback to the surgeon. For example, each different component, such as the implant, the implant host 10 (FIG. 2), and the implant positioning device 130, can be represented as a different color. In another example, the implant can be color-coded to indicate alignment in reference to the implant host 10. In this example, the color-coding can change from red to green (with various shades in between) to indicate where the implant is or is not properly aligned. At 635, the method 350 can continue with the control system 110 displaying the ideal implant location in reference to the various other 3-D representations, such as the implant host 10, the actual implant, and the implant positioning device 130. At 640, the method 350 can continue with the control system 110 adding a 3-D visualization of the implant host model to the display. In an example, the nature of the 3-D visualization displayed on the display device 140 can be controlled via foot control 170 (FIG. 2) by the surgeon. Controlling the display can enable the surgeon to scroll through various perspectives or control which components are displayed at a given time.

At 645, the method 350 can continue with the control system 110 (FIG. 2) generating audible alignment indicators. The audible alignment indicators can indicate implant alignment or implant positioning device 130 (FIG. 2) alignment according to the implant plan. Finally, at 650, the method 350 can conclude with the control system 110 generating haptic control signals to transmit to the implant positioning device 130. The haptic control signals can instruct the implant positioning device 130 to produce a vibration to provide tactile feedback to the surgeon. In an example, haptic tactile feedback may be used to indicate a particularly bad alignment of the implant positioning device 130 relative to the implant plan. Alternatively, haptic tactile feedback can be used to indicate a successful placement of the implant.

Example Implant Positioning Device

Figure 7:
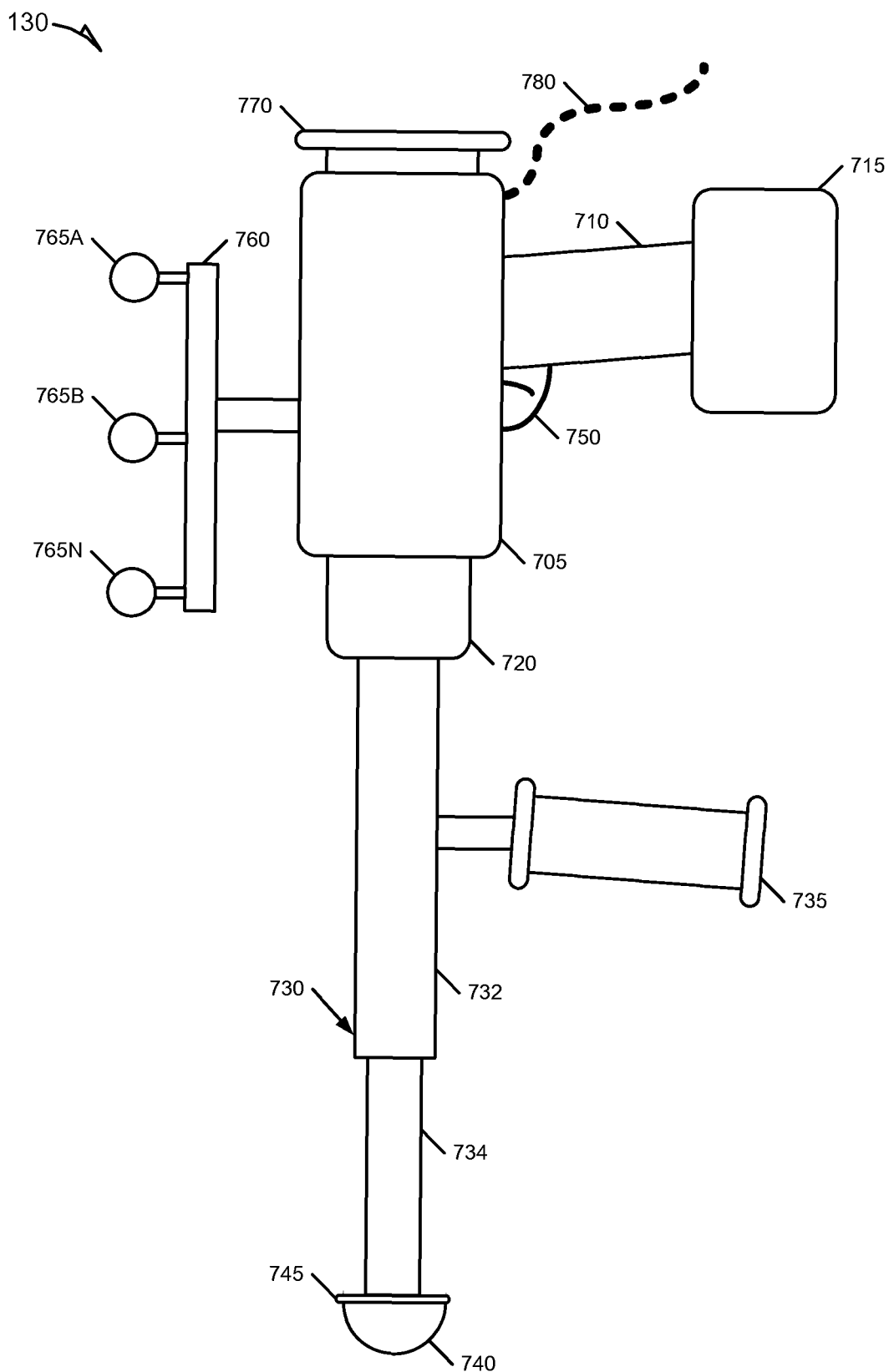
FIG. 7 is a diagram illustrating an implant positioning device, according to an example embodiment.

FIG. 7 is a diagram illustrating an implant positioning device 130, according to an example embodiment. In an example, the implant positioning device 130 can include components such as: a body 705, a handle 710, a battery 715, a chuck 720, a telescoping positioning arm 730, a stabilizing handle 735, an end effector 740, an implant retention device 745, a trigger 750, a tracking marker 760, a manual impact surface 770, and a communication link 780. The example implant positioning device 130 illustrated in FIG. 7 is a cordless computer-controlled impactor that can be used in THA procedures. Other implant positioning devices designed for other procedures may include similar components to those described in this example.

In this example, the primary components of the implant positioning device 130 include a main body 705, a handle 710, a battery (e.g., power supply) 715, a chuck 720, and a trigger 750. The main body 705 contains a motor and other control circuitry required to produce the desired impacts on the end effector 740. The chuck 720 can be configured to allow for inter-changeable positioning arms, such as telescoping positioning arm 730. In certain examples, the trigger 750 provides a manual override allowing the clinician to control the implantation process even while the implant positioning device 130 is receiving control signals from the control system 110.

In this example, the implant positioning device 130 includes a telescoping positioning arm 730. The telescoping positioning arm 730 includes a proximal fixed portion 732 and a distal moveable portion 734. In some examples, a stabilizing handle 735 can be affixed to the proximal fixed portion 732 of the telescoping positioning arm 730. The distal moveable portion 734 includes an end effector 740 affixed to the distal end. The end effector 740 can be configured to mate with an implant to reduce any potential damage to the implant during insertion. The end effector 740 can include a retention device 745 that can be configured to retain the implant in a fixed position relative to the end effector 740 during insertion.

The implant positioning device 130 can include a tracking marker 760 that allows the location and orientation of the implant positioning device 130 to be tracked by the tracking system 120 (FIG. 2). In an example, the tracking marker 760 can include three or more tracking spheres 765A ... 765N (collectively referred to as tracking sphere 765 or tracking spheres 765). The tracking spheres 765 can be active or passive devices. For example, active tracking spheres can include infrared LEDs enabling a tracking system, such as the commercially available OPTOTRAK® 3-D motion and position measurement and tracking system to track the implant positioning device 130 using infrared sensors. Other tracking systems may use cameras responsive to other wavelengths, which would indicate the use of tracking spheres emitting compatible wavelengths (or which reflect light in compatible wavelengths).

In this example, the implant positioning device 130 can include a manual impact surface 770. The manual impact surface 770 enables a surgeon to revert to manual impaction in situations where the computer-aided navigation and control is not functioning properly.

Finally, the implant positioning device 130 can include a communication link 780. In this example, the communication link 780 is illustrated as a wired connection. However, in other examples, the communication link 780 can be implemented over any suitable wireless protocol, such as IEEE 802.11 or Bluetooth, among others.

Figure 8A:
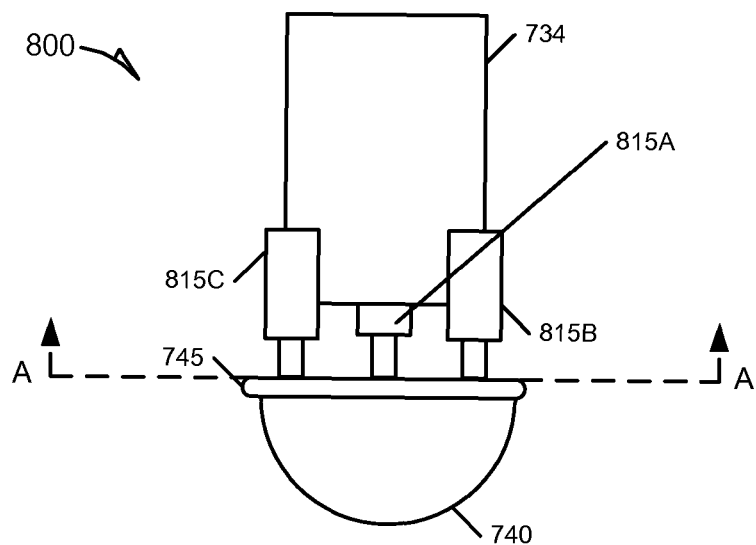
FIGS. 8A-8B are block diagrams illustrating an alternative end effector for the implant positioning device, according to an example embodiment.
Figure 8B:
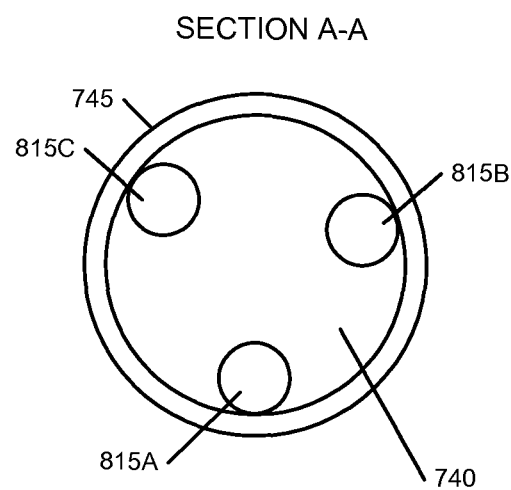

FIGS. 8A-8B are block diagrams illustrating an alternative end effector 800 for the implant positioning device 130, according to an example embodiment. The alternative end effector 800 can include a series of actuators 815A-815C (collectively referred to as actuators 815) positioned between the distal moveable portion 734 and the end effector 740. The actuators 815 can induce forces (e.g., impacts) on localized portions along the outer circumference of the end effector 740. As discussed above, actuators position to direct forces around the circumference of the end effector 740 can induce a desired rotation on the implant during impaction. FIG. 8B illustrates a section view of how actuators 815 can be arranged around end effector 740.

Figure 9:
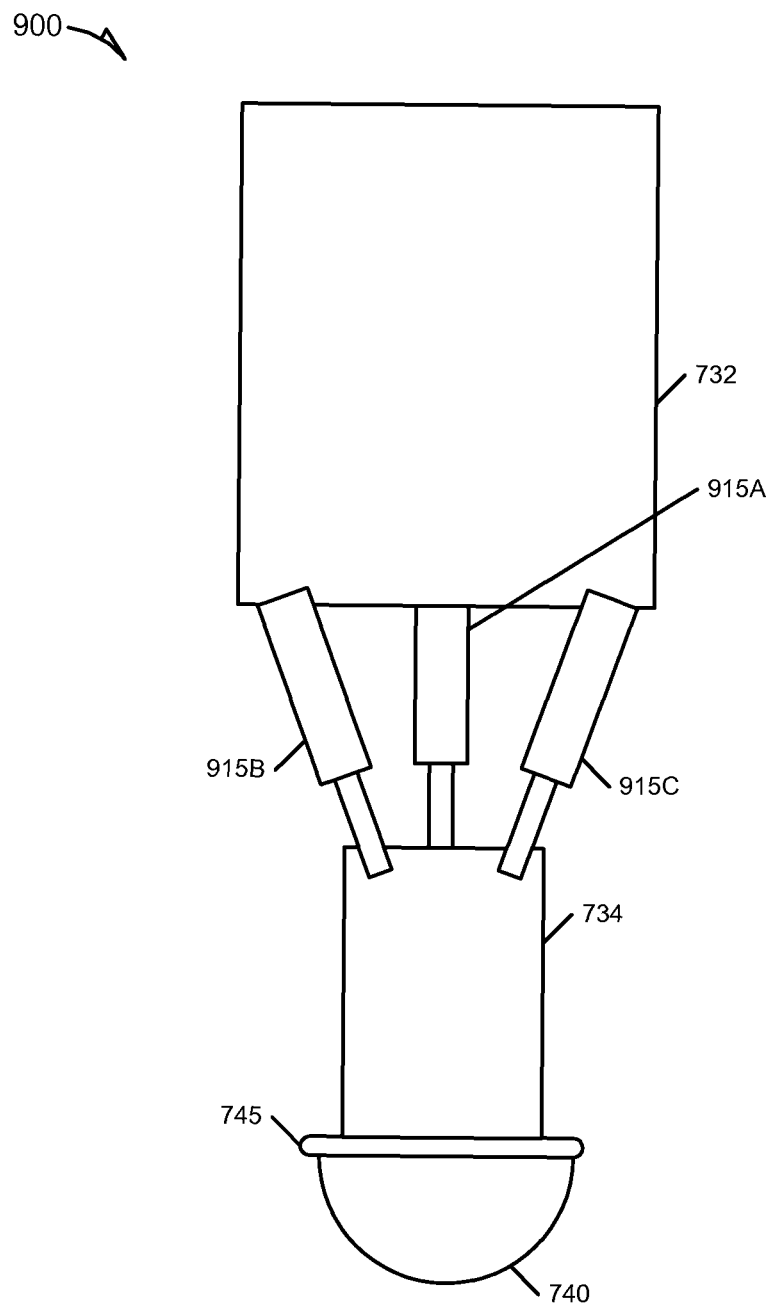
FIG. 9 is a block diagram illustrating another alternative arrangement for circumferential actuators, according to an example embodiment.

FIG. 9 is a block diagram illustrating another alternative arrangement for circumferential actuators 915A-915C, according to an example embodiment. In this example, the circumferential actuators 915A-915C are arranged between the distal moveable portion 734 and the proximal fixed portion 732.

Figure 10A:
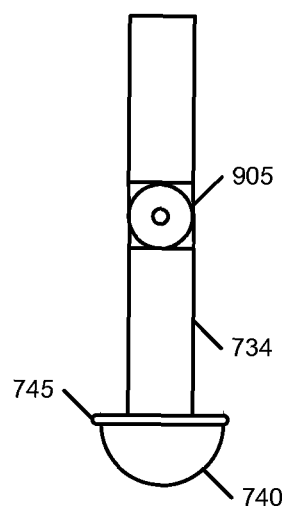
FIGS. 10A-10B are block diagrams illustrating an articulating portion of the powered impactor, according to an example embodiment.
Figure 10B:
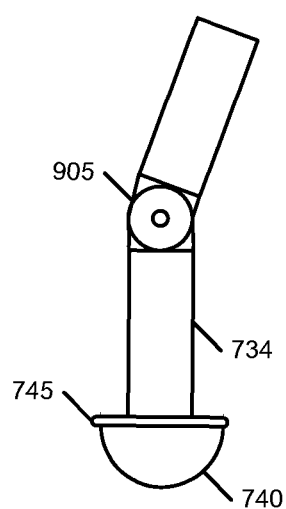

FIGS. 10A-10B are block diagrams illustrating an articulating portion of the powered impactor, according to an example embodiment. In this example, a portion of the telescoping positioning arm 730 can include an articulating joint 905. The illustrated example includes the articulating joint within the distal moveable portion 734 of the telescoping positioning arm 730. In another example, the articulating joint 905 can be included within the proximal fixed portion 732 of the telescoping positioning arm 730. The articulation joint 905 can be powered or manually manipulated to assist in positioning the implant during surgery.

Modules, Components and Logic

Certain embodiments of the computer systems described herein may include logic or a number of components, modules, or mechanisms. Modules may constitute either software modules (e.g., code embodied on a machine-readable medium or in a transmission signal) or hardware modules. A hardware module is a tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., APIs).

Electronic Apparatus and System

Example embodiments may be implemented in digital electronic circuitry, or in computer hardware, firmware, software, or in combinations of them. Example embodiments may be implemented using a computer program product, for example, a computer program tangibly embodied in an information carrier, for example, in a machine-readable medium for execution by, or to control the operation of, data processing apparatus, for example, a programmable processor, a computer, or multiple computers. Certain example embodiments of an implant positioning device 130 (FIG. 7) can include a machine-readable medium storing executable instructions to be performed by the implant positioning device 130.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry (e.g., a FPGA or an ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Medium

Figure 11:
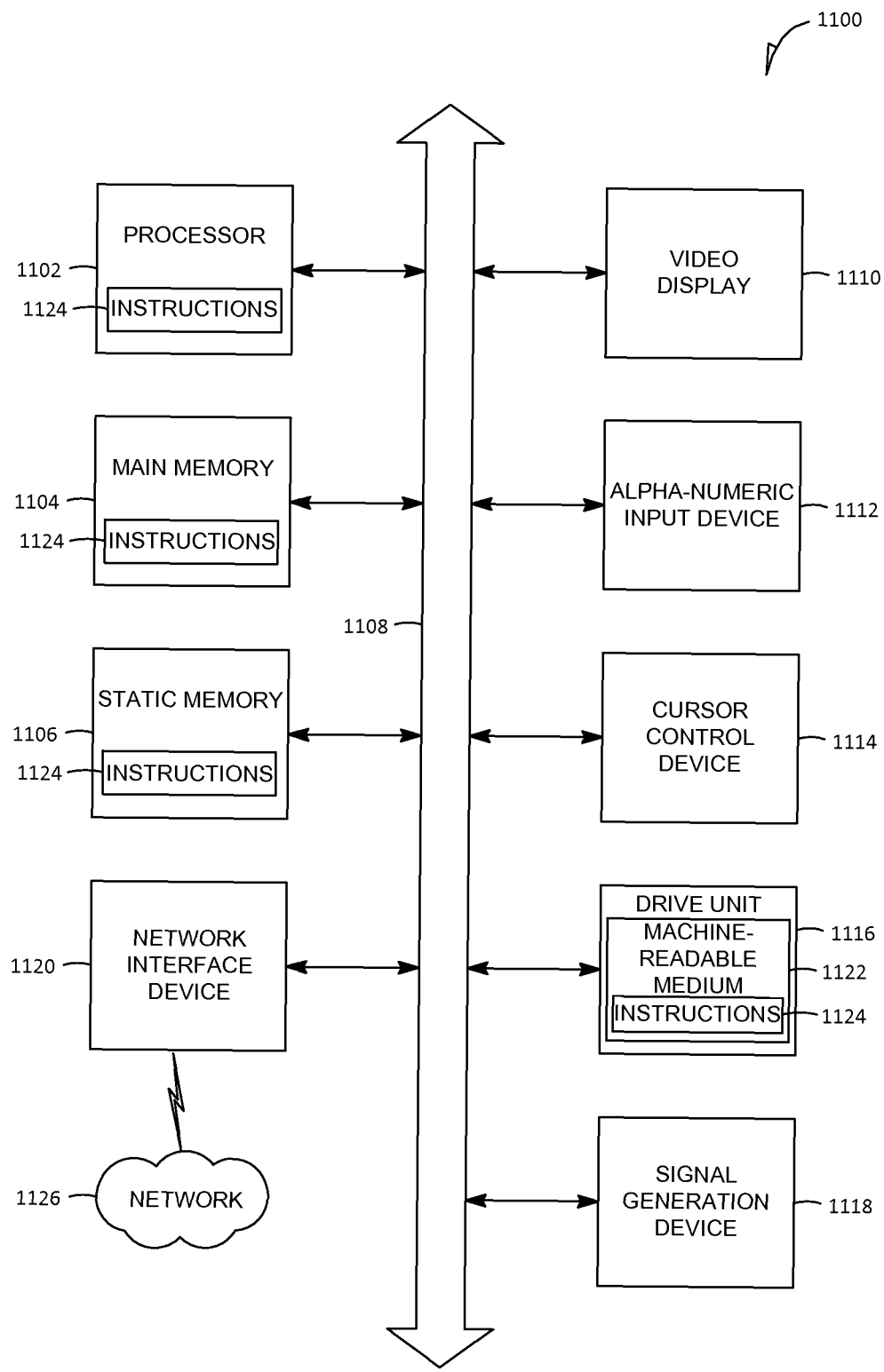
FIG. 11 is a diagrammatic representation of a machine in the example form of a computer system within which a set of instructions for causing the machine to perform any one or more of the methodologies discussed herein may be executed.

FIG. 11 is a block diagram of machine in the example form of a computer system 1100 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a PDA, a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1100 includes a processor 1102 (e.g., a central processing unit (CPU), a graphics processing unit (GPU) or both), a main memory 1104 and a static memory 1106, which communicate with each other via a bus 1108. The computer system 1100 may further include a video display unit 1110 (e.g., a liquid crystal display (LCD) or a cathode ray tube (CRT)). The computer system 1100 also includes an alphanumeric input device 1112 (e.g., a keyboard), a user interface (UI) navigation device (or cursor control device) 1114 (e.g., a mouse), a disk drive unit 1116, a signal generation device 1118 (e.g., a speaker) and a network interface device 1120.

Machine-Readable Medium

The disk drive unit 1116 includes a machine-readable medium 1122 on which is stored one or more sets of instructions and data structures (e.g., software) 1124 embodying or used by any one or more of the methodologies or functions described herein. The instructions 1124 may also reside, completely or at least partially, within the main memory 1104, static memory 1106, and/or within the processor 1102 during execution thereof by the computer system 1100, the main memory 1104 and the processor 1102 also constituting machine-readable media.

While the machine-readable medium 1122 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of example, semiconductor memory devices (e.g., erasable programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks. A "machine-readable storage medium" shall also include devices that may be interpreted as transitory, such as register memory, processor cache, and RAM, among others. The definitions provided herein of machine-readable medium and machine-readable storage medium are applicable even if the machine-readable medium is further characterized as being "non-transitory." For example, any addition of "non-transitory," such as non-transitory machine-readable storage medium, is intended to continue to encompass register memory, processor cache and RAM, among other memory devices.

Transmission Medium

The instructions 1124 may further be transmitted or received over a communications network 1126 using a transmission medium. The instructions 1124 may be transmitted using the network interface device 1120 and any one of a number of well-known transfer protocols (e.g., HTTP). Examples of communication networks include a LAN, a WAN, the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Thus, methods and systems for navigation and control of an implant positioning device have been described. Although the present invention has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be used and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments or examples have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended; that is, a system, device, article, or process that includes elements in addition to those listed after such a term in a claim are still deemed to fall within the scope of that claim. Moreover, in the following claims, the terms "first," "second," "third," and so forth are used merely as labels, and are not intended to impose numerical requirements on their objects.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

The invention claimed is:

1. An implant positioning device comprising:
 a positioning arm having a distal movable portion in mechanical communication with an articulating joint;
 an end effector, configured to contact an implant component during a surgical procedure, operably connected to a plurality of actuators positioned about an exterior periphery of the end effector;
 a motor mechanically connected to the plurality of actuators and the articulating joint, configured to:
  provide energy to each of the plurality of actuators, thereby allowing the plurality of actuators to impart a linear motion on the end effector; and
  provide energy to the articulating joint, thereby allowing the articulating joint to adjust an impact angle of the end effector; and
 a control circuit coupled to the motor and configured to:
  generate at least one motor control signal,
  transfer the at least one motor control signal to the motor, and
  as a result of the at least one motor control signal, cause the motor to move one or more of the plurality of actuators to produce one or more impacts on the end effector, wherein the plurality of actuators are configured to induce a rotation on the implant component during insertion of the implant component; and a communication device configured to:

establish a communication link with a surgical control system; and receive system control signals from the surgical control system, the system control signals for controlling the insertion of the implant component, wherein the system control signals comprise an impact frequency indication defining how frequently the implant positioning device is to impart the impact force to the implant component.

2. The device of claim 1, wherein the end effector comprises a retention device configured to retain the implant component in a fixed position relative to the end effector during the insertion of the implant component.

3. The device of claim 1, further comprising a tracking marker configured to be tracked by a tracking system, thereby providing for monitoring of a position of the implant positioning device during the surgical procedure.

4. The device of claim 1, wherein the motor is further configured to control extension of the positioning arm.

5. The device of claim 1, wherein the surgical procedure comprises a hip replacement surgery.

6. The device of claim 1, wherein the implant component comprises a prosthetic acetabular cup.

7. The device of claim 1, wherein the control circuit is configured to receive one or more parameters, the one or more parameters comprising an indicator that the implant positioning device is located within a planned position of the implant positioning device.

* * * * *